United States Patent
Sayler et al.

(10) Patent No.: US 7,020,560 B2
(45) Date of Patent: Mar. 28, 2006

(54) METHODS FOR CELL-BASED COMBINATORIAL LOGIC

(75) Inventors: Gary S. Sayler, Blaine, TN (US); James T. Fleming, Knoxville, TN (US); Bruce Applegate, West Lafayette, IN (US); Michael L. Simpson, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 09/949,015

(22) Filed: Sep. 6, 2001

(65) Prior Publication Data

US 2003/0044802 A1 Mar. 6, 2003

(51) Int. Cl.
G01N 21/00 (2006.01)
G01N 27/00 (2006.01)
G01N 33/48 (2006.01)

(52) U.S. Cl. ............... 702/19; 703/11; 435/3; 435/30; 435/173.1; 435/182

(58) Field of Classification Search ......... 703/11; 702/19–20
See application file for complete search history.

(56) References Cited

U.S. PATENT DOCUMENTS

2003/0049799 A1* 3/2003 Schwartz et al. .......... 435/69.7

FOREIGN PATENT DOCUMENTS

| WO | WO 99/42929 | 8/1999 |
| WO | WO 00/44094 | 7/2000 |

OTHER PUBLICATIONS

Yanagida et al., Journal of Biotechnology, vol. 79, (2000), pp. 53-61.*
Xia et al., Proceedings of the National Academy of Sciences, USA, vol. 94, pp. 11399-11404, Oct., 1997.*
Provisional application, U.S. Appl. No. 60/242,546.*

Hiratsuka, M., T. Aoki, and T. Higuchi, *Enzyme Transistor Circuits for Reaction Diffusion Computing, IEEE Transactions on Circuits and Systems-I: Fundamental Theory and Applications*, vol. 46, No. 2, Feb., 1999, pp. 294-303.

V.I. Merkulov, et al., *Patterned Growth of Individual and Multiple Vertically Aligned Carbon Nanofibers, Applied Physics Letters*, vol. 76, No. 24, Jun. 12, 2000, pp. 3555-3557.

V.I. Merkulov, et al., *Shaping Carbon Nanostructures by Controlling the Synthesis Process, Applied Physics Letters*, vol. 79, No. 8, Aug. 20, 2001, pp. 1178-1180.

B. M. Applegate, et al., *A Chromosomally Based tod-luxCDABE Whole-Cell Reporter for Benzene, Toluene, Ethybenezene, and Xylene (BTEX)Sensing, Applied and Environmental Microbiology*, vol. 64, No. 7, Jul. 1998, pp. 2730-2735.

J. T. Singleton, et al., *Induction of the tod Operon by Trichloroethylene in Pseudomonas putida TVA8, Applied and Environmental Microbiology*, vol. 64, No. 12, Dec. 1998, pp. 5049-5052; and.

B. Yurke, et al., *DNA Implementation of Addition in Which the Input Strands are Separate from the Operator Strands, BioSystems*, 52, (1999), pp. 165-174.

M.L. Simpson, et al., *Bioluminescent Bioreporter Integrated Circuits (BBCs): Whole-Cell Environmental Monitoring Devices, Society of Automotive Engineers, Inc.*, 00ICES-136 (1998).

\* cited by examiner

*Primary Examiner*—Mark K. Zeman (57) ABSTRACT

A method for cell-based combinatorial logic includes the steps of providing at least one genetically engineered cell, the genetically engineered cell having at least one transcriptional unit. The transcriptional unit includes a gene and a promoter, wherein application of a stimulus to the promoter results in the expression of a gene product. An energetic or chemical stimulus is applied to activate the promoter, wherein the detection of an output signal corresponds to the presence of a gene product. The cell can include a plurality of transcriptional units configured to form logic gates. The logic gates of a plurality of cells can be operably interconnected by release of output signals, such as chemical stimuli.

26 Claims, 8 Drawing Sheets

Component Designations

P = Promoter sequence for transcription of genes
G = Gene encoding polypeptide for regulatory or structural protein resulting in signal
S = Signal, output of gene action that is intra or intercellularly communicated or communicated to the integrated circuit
M = Modulator, physical or chemical input function as actuator to gene express

Base Case 1 - Chip-to-Cell Communication:

Inputs/Outputs

M1 = glucose
M2 = current
M3 = current
S1 = acyl homoserine lactone
S2 = light

Base Case 2 - Chip-to-Cell-to-Cell Communication:

Gene Regulation $P_1G_1G_2 = P_{l1}\ lux\ l_2$
$P_2G_2 = P_{e\text{-}}\ luxl_1\ R_1$
$P_3G_{4\text{-}7} = P_{lux\ l2/R2}\ lux\ CDE$
$P_4G_{6\text{-}10} = P_{e\text{-}}\ lux\ R\ AB$

| Regulator Proteins | Microorganisms | Normal Function of Regulated Gene(s) | Effectors (Inducer or Co-repressor) | Reference |
|---|---|---|---|---|
| Classic Gene Regulation Systems | | | | |
| LacI (negative) | *Escherichia coli* | Breakdown of ß-galactosides | Lactose and isopropylthigalactoside (gratuitous inducer) | Lin and Riggs, 1985 |
| CRP (positive) | *E. coli* | Catabolite repression | Cyclic AMP | Gaston et al., 1990 |
| TrpR | *E. coli* | Tryptophan synthetase | Tryptophan (co-repressor) | Zurawski et al., 1978 |
| Positive Regulators of LysR family (Schell et al., 1993) | | | | |
| AlsR | *Bacillus subtilis* | Acetoin synthesis | Acetate or pH | Renna et al., 1993 |
| NahR | *Pseudomonas putida* | PAH/Salicylate catabolism | Salicylate | Schell and Sukordhaman, 1989 |
| NhaR | *E. coli*, and *Salmonella enteriditis* | $Na^+$ - $H^+$ antiporter | $Na^+$ or $Li^+$ | Rahav-Manor et al., 1992 |
| TcbR | *Pseudomonas plasmid J51* | Chlorocatechol metabolism | 3-Chlorobenzoate | Van Der Meer et al., 1991 |
| Positive Regulators of the Tol catabolic pathway (Burlage et al., 1989) | | | | |
| XylR | *Pseudomonas Tol plasmid* | Upper pathway: toluene to benzoate | Toluene, m-xylene | Worsey et al., 1978 |
| XylS | *Pseudomonas Tol plasmid* | Lower pathway: benzoate to catechol | Benzoate, m-toluate and p-toluate | Worsey et al., 1978 |
| Positive regulation of the ß-ketoadipate pathway (Parke, 1997) | | | | |
| PobR | *Agrobacterium tumefaciens* | Conversion of 4-hydroxybenzoate to protocatechuate | 4-hydroxybenzoate | Parke, 1995 |
| PcaQ | *Agrobacterium tumefaciens* | Conversion of protocatechuate to ß-ketoadipate | B-carboxy-cis, cis-muconate and y-carboxy-muconolactone | Parke, 1996 |
| PcaR | *Agrobacterium tumefaciens* | Conversion of ß-ketoadipate | ß-ketoadipate and dicarboxylate adipate (gratuitous inducer) | Parke, 1997 |
| Two Component Signal Transduction: Tod system | | | | |
| TodST | *Pseudomonas Putida* | Metabolism of Toluene | Toluene | Lau et al., 1997 |
| Quorum-Sensing Transcriptional Regulators (Fuqua et al., 1996) | | | | |
| LuxI | *Vibrio fischeri* | Synthesis of N-3 (oxohexanyl)-homoserine lactone | | Eberhard et al., 1981 |
| LuxR | *Vibrio fischeri* | *lux* genes-bioluminescence | N-3-(Oxoxhexanoyl)-homoserine lactone | Stevens et al., 1994 |
| Gene Regulation of Metal Ions | | | | |
| Fur (negative) | *E. coli* | Production of siderophores | $Fe^{+2}$ (co-repressor) | Hantke, 1982 |
| MerR (negative and positive) | *Shigella flexneri* (Tn21), *P. aeruginosa* (Tn501), and plasmid pDU1358 | Reduction of $Hg^{+2}$ to Hg | $Hg^{+2}$ (and sometimes organomercurials)-both co-repressor and activator | e.g., Ross et al., 1989 |
| ArsR (negative) | *E. coli* | *Efflux systems* | Arsenite, arsenate, antimonite and bismuthate (inducers) | Mobley et al., 1983 |

FIG. 9
Page 1-2

| Regulator Proteins | Microorganisms | Normal Function of Regulated Gene(s) | Effectors (Inducer or Co-repressor) | Reference |
|---|---|---|---|---|
| | | | | |
| Redox Sensitive Transcriptional Regulators (Bauer et al., 1989) | | | | |
| SoxR | E. coli | Reduces superoxides | Oxidative stress conditions | Hildalgo et al., 1985 |
| OxyR | Salmonella typhimrium and E. coli | Controll expression of 9 stress-response proteins | e.g., Hydrogen peroxide | Christman et al., 1985 |
| Temperature Sensitive Transcriptional Regulator | | | | |
| cI857 | Phage PhiX174 | Lysis of E. coli | Repressed up to 30 °C | Remaut et al., 1981 |
| CI857 | Phase PhiX174 | Lysis of E. coli | Repression (increased) 36 °C | Jechlinger, W. et al., 1999 |
| Light Sensitive Transcriptional Regulators | | | | |
| RecA | λ-phage | UV damage repair | Ultraviolete radiation | Elasri and Miller, 1998 |
| RcaD | Fremyella disloisphon | Absorbs red light | Red light | Sobszyk et al., 1994 |
| RecAB | Fremyella diplosiphon | Absorbs green light | Green light | Sobczyk et al., 1994 |

FIG. 9
Page 2-2

| IC Temperature | Response to Chemical Inputs | | | | | | |
|---|---|---|---|---|---|---|---|
| | T | B | S | BT | BS | TS | BTS |
| 25 °C | 1 | 0 | 0 | 1 | 1 | 0 | 1 |
| 32 °C | 0 | 1 | 0 | 1 | 0 | 1 | 1 |
| 42 °C | 0 | 0 | 1 | 0 | 1 | 1 | 1 |

T = TCE  B-benzoate  S=salicylate

FIG. 10

| Compound(s) | 25 °C Cell output IC input (± light) | IC output Cell input (temp) | 32 °C Cell output IC input (± light) | IC output Cell input (temp) | 42 °C Cell output IC input (± light) |
|---|---|---|---|---|---|
| TCE | Light | 32 °C | No-light | 42 °C | No-light |
| benzoate | No-light | 32 °C | Light | 42 °C | No-light |
| salicylate | No-light | 32 °C | No-light | 42 °C | Light |
| TCE benzoate | Light | 32 °C | Light | 42 °C | No-light |
| TCE salicylate | Light | 32 °C | No-light | 42 °C | Light |
| benzoate salicylate | No-light | 32 °C | Light | 42 °C | Light |
| TCE benzoate salicylate | Light | 32 °C | Light | 42 °C | Light |

FIG. 11

METHODS FOR CELL-BASED COMBINATORIAL LOGIC

STATEMENT REGARDING FEDERALLY SPONSORED RESEARCH OR DEVELOPMENT

Not Applicable

FIELD OF THE INVENTION

The invention relates to in-vivo cellular information processing devices and methods to use the same.

BACKGROUND OF THE INVENTION

Conventional information processing devices utilize silicon-based technology which has certain known fundamental limitations when used to form integrated devices. Such devices are fabricated using a top down approach. In the microelectronics industry, for instance, lithographic techniques are used to etch away at a semiconducting (e.g. silicon) crystal or otherwise define deposited layers to form micrometer or even sub-micrometer size devices and circuitry. As device features have become finer, the number of devices that can be crammed onto a chip has been doubling approximately every 18 to 24 months for at least the last two decades. Smaller devices provide lower cost, higher speed and/or higher processing power. The vast majority of chips fabricated form digital devices, such as microprocessors, computers, memory devices and a wide variety of other related devices.

Digital technology can be explained with Boolean logic gates, such as NOT gates. The simplest of all gates is the NOT which functions as a simple inverter. The Not gate takes a single input signal and produces the opposite value as its output. Thus, true becomes false, and false becomes true. Boolean logic gates are devices that operate on signals with two possible values, such as true and false, or 1 and 0. An AND gate has two or more inputs and one output, the output being true only if all the inputs are true. An OR gate is similar except that the output is true if any of the inputs are true.

Chip makers will likely be unable to extend the current miniaturization trend for another decade. As features shrink into the several hundred nanometer range, chips will likely not be able to operate, or at least not operate reliably. Redundancy is generally not provided for integrated electronic devices, resulting in potential catastrophic failures in the field for entire integrated circuits due to a single isolated failures of discrete devices or a single connection between discrete devices. Connectivity of various discrete devices becomes increasingly problematic as device sizes have decreased. Moreover, the cost of constructing new fabrication lines for each new generation of chips is expected to become prohibitive. As a result, there is a need to develop alternative technologies for the fabrication computers and other integrated devices.

Organic molecules, including cellular molecules from living cells have been found to be generally resistant to a broad range of ambient and externally applied conditions and possess the potential to create information processing devices having high density levels without many of the above-mentioned limitations of silicon based technology. However, attempts to develop information processing capabilities based on organic molecules has had little success because many difficult challenges have been simultaneously encountered by researchers. For example, challenges arose in areas relating to stimulation of a plurality of molecules, detection of output signals generated by the molecules, as well as lack of design tools when utilizing such molecules analogous to computer aided design (CAD) which is commonly used to design electronic devices.

Some devices have incorporated the use of non-cellular organic molecular material in combination with electrical devices and systems. For example, International Application No. PCT/US00/01360 to the University of South Carolina, describes a nanocell molecular computer.

The described nanocell computer contains a two-dimensional array of a few hundred metallic nanoparticles bridged by a somewhat higher number of functional organic molecules. These functional molecules connect the nanoparticles to input and output leads arranged around the periphery of the nanocell. Thus, different combinations of input and output leads allows addressing different current-carrying pathways.

The arrangement of the nanoparticles and bridging molecules in these pathways is initially random. By applying voltage pulses to various combinations of input and output leads, molecules (switches) can be set to "on" or "off" states in groups. Which switches are on (conducting) and which are off (insulating) will not be initially known. In a trial-and-error fashion, computer algorithms repeatedly test and tinker with a pathway (using voltage pulses of different magnitudes) until the pathway performs the desired operation, such as that of a logic gate or adder. Thus, in view of the required programming of each switch, the teachings of the nanocell computer described by PCT/US00/01360 are not well suited for use in forming devices having any significant level of integration.

Another example of related technology is a biomolecular switching device called an enzyme transistor. Hiratsuka, M., T. Aoki, and T. Higuchi (1999) IEEE Trans. On Cir. and Sys. -I: Fund. Theory and Appl. 46 (2), 294–303 (Hiratsuka). The enzyme transistor described by Hiratsuka can be viewed as an artificial catalyst which selects a specific substrate molecule and chemically transforms it into a specific product. The catalytic activity of particular enzymes are each regulated by a specific effector.

The enzyme devices formed can be considered to be analogous to a bipolar junction transistor having a chemical substrate acting as an emitter, an enzyme acting as a base and a product acting as a collector. An integrated enzyme device can feature multiple enzyme devices which can be coupled together to form a network of biochemical reactions defined by the molecular selectivity of the enzyme transistors. Multiple enzyme transistors can be connected together by chemical diffusion, rather than a physical structure as in electronic integrated circuits for device-device interaction. Thus, wire-free computing circuits can be realized. The information is coded into molecular agents and then discriminated by the selectivity of the enzyme transistor. Hiratsuka describes formation of logic circuits, such as a NOR gate. Although Hiratsuka suggests the simple devices formed could be extended to more complex circuit designs, he provides little or no guidance in producing such devices.

Thus, available alternative devices such as the enzyme transistor proposed by Hiratsuka have not produced or cannot be expected to allow production of highly integrated information processing devices. Accordingly, the teachings of these available alternative devices are unable to approach or exceed integration levels offered by conventional silicon based devices which perform analogous functions.

SUMMARY

The invention harnesses the computing power of living cells and uses cellular processing to implement biochemical logic circuitry based on intra- and inter-cellular processes. Cellular transcriptional logic modules have been devised that mimic the three basic electronic AND, OR and XOR gates. From these gates, a variety of devices can be formed, such as microprocessors. Cellular analogues of these three logic gates link transcriptional induction to the creation of a specific gene product or effect. The ability to create high-density logic circuits using the cellular transcriptional machinery permits the creation of living microprocessors, which do not require hard wired interconnections between individual logic devices.

A cellular logic device includes a substrate and a structure for providing stimulus to a plurality of discrete portions of the substrate, the substrate having at least one biological cell disposed thereon. The cell includes at least one transcriptional unit, the transcriptional unit having a gene and a promoter. The application of a stimulus to the promoter results in the expression of a gene product. The gene product(s) preferably confer a bioluminescent output, although it may be any product producing a detectable output. Alternatively, the gene product can be a detectable product itself. A structure for detecting the presence of the gene product, such as an optical detector, is also provided. The device can be placed in a package, the package formed from either sol-gel or a silicone elastomer.

Promoters can be responsive to electrical, thermal and chemical stimuli. In a preferred embodiment, a current inducible promoter is provided which is responsive to electrical stimuli. In the case of chemically inducible promoters, the chemical stimuli can be delivered by a microfluidic device. In a preferred embodiment, the cell is a genetically engineered cell and includes a current inducible promoter.

The device can include two or more transcriptional units and form OR, XOR and AND gates. A first transcriptional unit includes a first gene and a first promoter while the second transcriptional unit includes a second gene and a second promoter. Both promoters can have equivalent gene transcription effects. In the case of an XOR gate, the first gene can be joined to its promoter in a sense orientation and the second gene can be joined to the second promoter in an anti-sense orientation, the second gene positioned upstream from the first gene. In the case of an AND gate, the synthesis of a messenger RNA strand can be linked to a transcriptional sigma factor required by RNA polymerase to recognize a correct DNA coding sequence.

The device can include a plurality of communicably connected discrete logic devices each formed from at least one transcriptional unit. This multiple gate device can form a microprocessor or a memory, including a non-volatile memory device. The substrate can include an electronic integrated circuit (IC) formed thereon. The IC can have a plurality of independently controllable electrically conductive nanofibers disposed on the substrate bounding the portions. The electrically conductive nanofibers can be graphite fibers. In this embodiment, the cell is a genetically engineered cell including a current inducible promoter and a gene that expresses product(s) that preferably confer a bioluminescent output, although it may be any product producing a detectable output or a being detectable product itself. The structure for detecting the presence of the gene product can be an optical detector. A kit includes an in-vivo cellular logic device and instructions for its use.

A method for processing data includes the steps of providing at least one genetically engineered cell, the genetically engineered cell having at least one transcriptional unit. The transcriptional unit includes at least one gene and one promoter. Application of an appropriate stimulus to the promoter modifies gene expression levels, and can result in the expression of a gene product. The applying step can include independently controlling application of the energetic or chemical stimulus to a plurality of the transcriptional units. The method includes a detection step for presence of at least one output signal related to the presence of the gene product. Gene products preferably result in bioluminescence to facilitate detection. In a preferred embodiment, the applied energetic stimuli includes electrical current and the promoter or promoters include at least one current inducible promoter.

A plurality of transcriptional units can be provided configured to form a plurality of interconnected logic gates, the respective logic gates chemically communicating information (e.g. through chemical diffusion) between respective logic gates. Since a given cell can provide multiple gates, gate interconnectivity can be both intracellular and intercellular. The method can include electrically inducing expression of a first gene product from a first logic gate. The first gene product induces production of at least one diffusible product which can induce expression of gene products from other logic gates. Electrical current is applied to at least one of the plurality of transcriptional units. An electronic IC can preferably be used for application of the electrical current to induce expression of a gene product from at least one transcriptional unit, the integrated circuit having a plurality independently controllable electrically conductive nanofibers disposed thereon.

A method for detection of an analyte includes the steps of contacting a sample suspected of containing the analyte with a cellular logic device. The cellular device provided includes a substrate and a structure for providing stimulus to a plurality of discrete portions of the substrate, the substrate having at least one biological cell disposed thereon. The biological cell includes at least one transcriptional unit, the transcriptional unit having a gene and a promoter. A structure for detecting the presence of the gene product, is also provided. The presence of an output signal from said cellular logic device is monitored, wherein the presence of the output signal is indicative of the presence of said analyte. The method can include the step of determining the concentration of the analyte. The sample can be an environment sample. The environmental sample can include at least one chemical toxin.

BRIEF DESCRIPTION OF THE DRAWINGS

The drawings form part of the present specification and are included to further demonstrate certain aspects of the present invention. The invention may be better understood by reference to one or more of the following drawings in combination with the detailed description of specific embodiments presented herein.

DETAILED DESCRIPTION

As used in the specification and the appended claims, the singular forms "a", "an" and "the" include plural referents unless the context clearly dictates otherwise. Thus, for example, reference to "a stimulus" includes mixtures of stimuli, and the like.

In this specification and in the claims which follow, reference will be made to a number of terms which shall be defined herein to have the following meanings:

The term "bioreporter" is used to refer to one or more living cells which produce a measurable output response based on one or more input stimuli, such as chemical or electrical stimuli.

The term "cellular transcription" is used to refer to the process by which messenger RNA is synthesized from a DNA template resulting in the transfer of genetic information from the DNA molecule to messenger RNA.

The term "gene cassette" is used to refer to a pre-existing structure into which an insert can be moved and may be used to refer to certain vectors (defined below).

The term "plasmid" is used to refer to circular, double-stranded unit of DNA that replicates within a cell independently of the chromosomal DNA. Plasmids are found in bacteria and are commonly used in recombinant DNA research to transfer genes between cells.

The terms "transcriptional unit" or "gene transcriptional unit" refer to the combination of at least one gene and at least one promoter.

The term "translation" is used to refer to the process by which messenger RNA directs the amino acid sequence of a growing polypeptide during protein synthesis.

The term "truth table" is used to refer to a listing of values of a proposition that result from all the possible combinations of the values of its components.

It would be desirable to harness the chemical processing performed by living cells to form highly integrated devices because cells have tremendous potential information process capability. For example, the processing power of *E. coli* cells has been estimated as being equivalent to a 9.2 Mbit memory for a 1 $\mu^2$ cell with 4.6 Million base-pair chromosome, since the four possible combinations at each base pair site equates to 2 bits per base-pair. *E coli* also has multiple chemical and physical signal I/O ports. Tapping even a significant percentage of the above information processing power of cells, such as *E. coli*, could permit the formation of highly reliable, extremely densely packed cell based integrated devices.

The invention uses living whole cells to implement functions associated with conventional electronic transistor gates. As noted above, living cells have a high capacity for storing and processing information on their genomes. More specifically, genetic control, which switches genes on and off and results in gene expressed products may be used to perform functions analogous to information processing currently performed by conventional electronic digital circuitry, such as microprocessors. Use of continuous level signals derived from gene expressed products can also permit the formation of certain analog circuits.

The construction of in-vivo logic gates permits information processing by whole cells. In a preferred embodiment of the invention, the whole cells are genetically-engineered cells. Genetically engineered cells can be used, for example, to create or enhance the response of promoters to one or more stimuli so as to express or increase the level of gene expression of certain gene products in response to a particular applied stimuli. The ability to create high density logic circuits using cellular transcription permits the creation of living microprocessors that can use diffusion, such as chemical diffusion, rather than rely on hard wired interconnections for signals to be transferred between devices, such as discrete logic gates. Such biocomputers or information processing devices can potentially provide massive parallel computation on a micrometer scale that will not be approachable with semiconductor (e.g. silicon) technology in the foreseeable future.

The functions of the most complex semiconductor based microprocessors may be described as circuits consisting of combinations of the three basic logic gate modules being AND, OR and XOR gates. Cellular embodiments of these three logic gates that link transcriptional induction to the creation of a specific gene product or effect can be constructed using the invention. Genetic engineering techniques can be used to enhance information processing efficiency of existing cells to further improve gate density.

The International Technology Roadmap for Semiconductors predicts that by the year 2014 logic transistor density will reach 664M/cm$^2$. Assuming 4 transistors/logic function, 1 $\mu$m$^2$ of Si will contain a 245 bit memory or 1.66 simple logic functions. A simple 1 $\mu$m$^2$ bacterial cell has several hundred promoters that control gene expression. Different bacteria contain different regulated promoters and different numbers of promoters. If only a fraction of these promoters are exploited for logic modules, the density of logic gates that is achievable far exceeds that presently predicted using semiconductor (e.g) silicon technology.

As in the expression of a protein by any gene, synthesis of an enzyme is a two-stage process. First, DNA is transcribed into messenger RNA by the enzyme RNA polymerase. Transcription is the process by which the messenger RNA is synthesized from a DNA template resulting in the transfer of genetic information from the DNA molecule to the messenger RNA. The messenger RNA is then translated into a protein by ribosomes. Translation is the process by which messenger RNA directs the amino acid sequence of a growing polypeptide during protein synthesis.

The translation process is controlled at the transcription stage. Before a gene can be transcribed, RNA polymerase must bind to the DNA at a promoter, which is located upstream of the gene. The polymerase must then travel along one strand of the DNA double helix, reading off the sequence of nucleotide bases and assembling a complementary strand of messenger RNA. One mechanism of control prevents transcription by physically blocking the progress of the RNA polymerase molecule. The blocking can be done by an appropriate repressor protein, which can bind to the DNA downstream of the promoter region and prevent the RNA polymerase from binding to the DNA.

Gene transcription units comprising a gene and a promoter can be supplied by living cells. Application of an appropriate input stimulus, such as a chemical or energetic stimulus to the promoter results in expression of a gene product which can be used as an output of the transcriptional unit. Thus, transcriptional units can be used as a biological building block to form a variety of biochemically based devices.

Biochemical devices based on transcriptional units can be used to create digital (e.g. logic) or analog circuits and provide the capability of massively parallel organization. For example, linked logic circuits can be used to form more complex digital devices, such as microprocessors. A single transcriptional unit can include a promoter ($P_n$) that is inducible or controllable by one or more stimuli and a gene (G). The gene sequence is a DNA sequence that codes for a gene product. Promoters may be induced by various stimuli, such as thermal, optical, chemical and electromagnetic (e.g. electrical and magnetic) stimuli. Cells naturally contain promoters which are inducible by a variety of stimuli. However, in a preferred embodiment of the invention, selected promoters are inserted into genes, the promoters being stimulated by one or more desired stimuli. The insertion can be provided by available genetic engineering techniques.

In a most preferred embodiment of the invention, cellular devices include promoters which are electrical current inducible. Being electrically inducible, conventional electronic integrated circuit technology, as described in detail later, can be used for independently applying controlled stimuli to a plurality of discrete portions of the device, the discrete portions each having at least one transcriptional unit. To employ promoters that are highly sensitive to electrical current, current inducible promoters can be inserted into an existing gene.

Genes that are differentially expressed by electrical stimulation can be identified by screening of bacterial genes, for example the 4,107 genes of *B. subtilis*. Using high and low amperages for current stimulation of the *B. subtilis* genes, at least 13 genes that are differentially expressed have been detected. Exemplary comparison stimulations are, for example, an 80 mA current at 32V for 20 min and a 5 mA current at 3V for 10 min. The promoters corresponding to the identified genes can be isolated and used as heterologous promoters in the disclosed transcriptional units for the logic circuits described herein.

If the transcriptional unit expresses a gene product, the expressed gene product may include a regulator or an enzyme. In the case of an enzyme product, the output of the transcriptional unit is a signal (S) that can be detected as the enzyme itself or through detection by observing activity of the enzyme using methods including spectroscopic, photochemical, biochemical, immunochemical, electrical, optical (e.g. bioluminescence) or genetic means. In a preferred embodiment of the invention, bioluminescence is detected. A gene product which confers a bioluminescent output permits detection using high resolution optical detectors such as CCD detectors.

Figure 1:
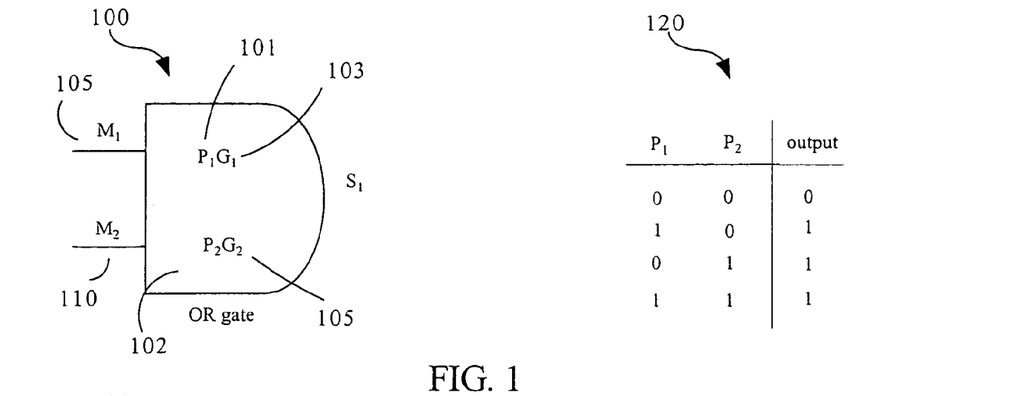
FIG. 1 Illustrates an OR gate, according to an embodiment of the invention.

An in-vivo OR gate 100 can be formed from two inducible promoters 101 and 102 linked with genes 103 and 104, respectively, having identical gene transcription effects, is illustrated in FIG. 1 along with its associated truth table 120. If inducer inputs M1 (105) and M2 (110) induce either promoter 101 or 102 to become stimulated, a functional protein will be expressed by OR gate 100. The functional protein will not be produced only when neither promoter (101, 102) is induced. An output signal can be detected either from the expressed gene product or a characteristic associated with the expressed gene product (e.g. bioluminescence).

There are at least two strategies for implementing OR gate 100. Two promoters can be used which have identical gene transcriptional effects, but respond to two different inducers. Another strategy involves use of a single promoter that responds in a similar manner to two different inducers. For example, the latter strategy can be implemented using a tod-lux fusion in *Pseudomonas putida* TVA8. This operon can be induced by both trichloroethylene (TCE) and toluene. The result is the production of bioluminescence if either inducer is present, thus realizing the required function of OR gate 100.

Figure 2:
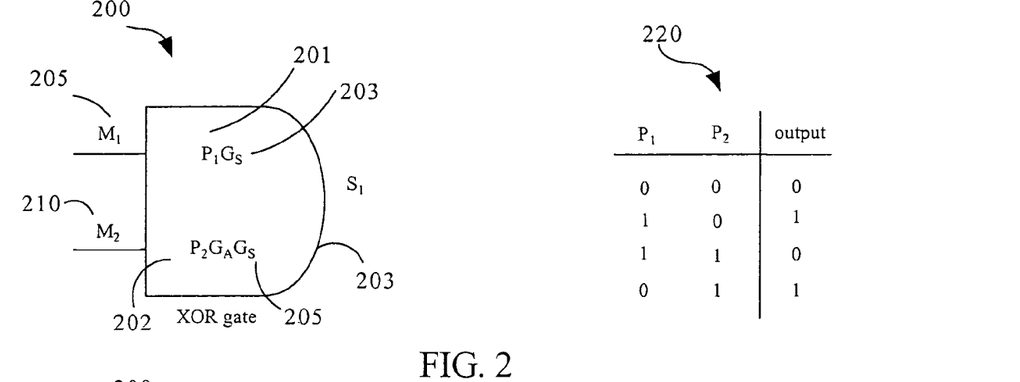
FIG. 2 Illustrates an XOR gate, according to an embodiment of the invention.

An in-vivo XOR logic gate 200 can be formed from two promoters 201 and 202 linked with genes 203 and 205 respectively, the genes having different gene transcription effects, as illustrated in FIG. 2 along with its associated truth table. If either of the respective promoters 201 and 202, but not both promoters, are stimulated by respective inducers 205 and 210, a functional protein will be expressed by XOR gate 200 and result in detectable output signal 215. In the embodiment of XOR gate 200 shown in FIG. 2, sense 203 and anti-sense 205 genes and resulting modes of regulation permits formation of the XOR device.

For example, an XOR gate 200 can be constructed on two transposable plasmids in *E. coli*, which can be integrated into the *P. fluorescens* genome. Two effector molecules control the behavior of the genetically engineered XOR gate. Salicylate, a derivative of naphthalene, is known to be a competent inducer of the nahR/nahA promoter. Salicylate induction can promote the transcription of a genetically modified luxAB gene to provide the catalytic luciferase necessary for bioluminescence. The second gene construct can contain a tetR/promoter upstream from the luxAB gene that is also 5' and 3' modified, but modified to operate differently from the first gene construct, as described later. Tetracycline (M2) can then act as the second effector molecule.

With only one of the salicylate 205 and tetracycline 210 inducers present, the expression of the luxAB gene will generate light if the co-effectors $O_2$, $FMNH_2$ and n-decanal (a synthetic analog of myristyl aldehyde) are also present. This light producing event is analogous to the expected output of a XOR logic gate when only one of the two XOR inputs is present. After approximately two hours in the presence of salicylate (M1) and without the presence of tetracycline (M2), the *E. coli* cells described above containing the respective luxAB genes emit light at 1,474 counts per second, a 4.5 fold increase over *E. coli* cells not exposed to salicylate.

When both inducers salicylate 205 and tetracycline 210 are present, the complementary ends of the two different luxAB RNA transcripts tend to anneal, thereby preventing access to the ribosomal binding site and consequent translation, ABlux production and associated light production. Modifications to the 5' and 3' ends of the two luxAB genes are specifically designed such that in the event that both luxAB RNA transcripts are present they will hybridize along these modified extensions. The 5' "sense" extension of the first luxAB RNA transcript anneals to the 3' "antisense" extension of the second luxAB RNA transcript, and this also applies to the 5' end of the second transcript and the 3' end of the first transcript. Hybridization at the 5' end of the mRNA can prevent ribosome access to the ribosome binding site, hindering expression of the luciferase. A consequence of minimizing the amount of luciferase in the cell is the generation of less light when n-decanal is provided to the *P. fluorescens* cells. Consequently, a false output is expressed by the XOR logic gate 200 which may be detected.

Figure 3:
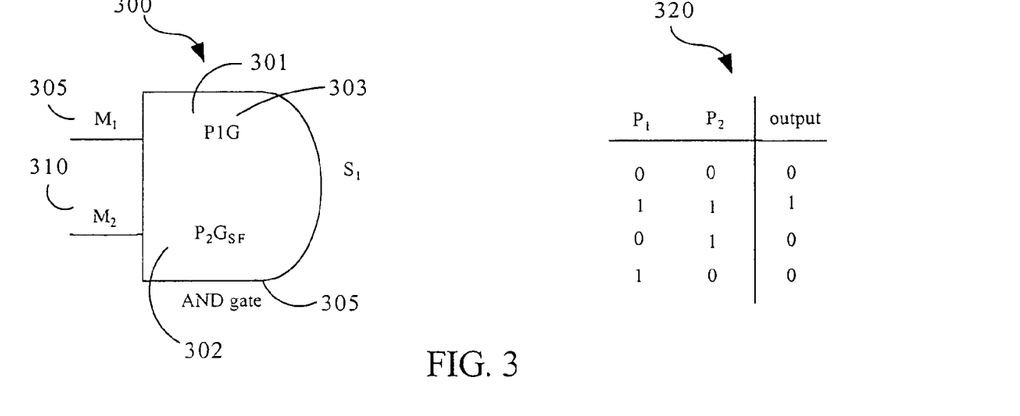
FIG. 3 Illustrates an AND gate, according to yet another embodiment of the invention.

An in-vivo AND logic gate 300 can be formed from two promoters 301 and 302 linked with genes 303 and 305, respectively, having different gene transcription effects, as illustrated in FIG. 3 along with its associated truth table 320. In one embodiment, AND gate 300 is constructed by linking the synthesis of the RNA strand to the synthesis of the transcriptional sigma factor (SF) required by the RNA polymerase to recognize the correct DNA coding sequence. In this case, the luminescent protein will be synthesized only if both promoters 301 and 302 are stimulated by respective inducers 305 and 310.

An AND gate can be formed in a number of ways. For example, *P. putida* containing a nahR sal (salicylate induced) promoter regulatory cartridge can be fused to the luxAB gene which codes for luciferase and the todST tod promoter (toluene induced regulatory cartridge fused to the luxCDE genes). In this embodiment, light is produced only when both toluene and salicylate are present due to expression of genes necessary for bioluminescence. Either of these chemically inducible promoter cartridges may be interchanged with a current inducible promoter.

Alternatively, AND gate 300 can be formed from genetically altered *E. coli*. The AND gate 300 can be assembled in plasmids in *E. coli*, and transposed into *P. fluorenscens*. In particular, AND gate 300 can be constructed using luxCD-ABE operator ($O_{lux}$), tetracycline regulatory protein (tetR) and operator ($tet_{PR}$), luxR protein and luxCDABE gene cassette for bioluminescence. Genes can be inserted using PCR, cloned into PCRII vectors (Invitrogen Corporation, Carlsbad, Calif. 92008) and subsequently cloned into MiniTNS Transposons for chromosomal insertion into *P. fluorenscens* 5R.

Homoserine lactone (HSL) is supplied in the extracellular media as an input to AND gate 300. HSL forms an autoinducer complex with LuxR. The luxCDABE regulatory gene forms an autoinducer complex with HSL. The second externally induced input can be tetracycline, an antibiotic that depresses the luxR promoter by binding to the tetratcycline regulatory protein (tetR). The luxCDABE genes are upregulated by the autoinducer complex to produce light.

The presence of tetracycline can cause the removal of a repressor from the operator that controls both the tetR gene and the luxR gene. Acyl-honmoserine lactone (AHL) will then bind to the LuxR protein, which in turn will bind to the operator for the luxCDABE genes resulting in expression of a luminescent protein and ultimately in the production of light. In view of the above mechanism, the presence of either inducer (teracycline or HSL) alone results in no light production.

Combinations of the above described OR, AND and XOR gates permit realization of a wide variety of combinatorial functions. Depending on the overall circuit design requirements, each logic gate may exist in a separate cell or many gates can occupy the same cell, the latter permitting a higher level of parallelism without hardwire interconnects linking individual logic gates. Thus, the invention provides communicable linkage between discrete gates without the use of electrically conductive wires required in conventional semiconductor processing.

Figure 4:
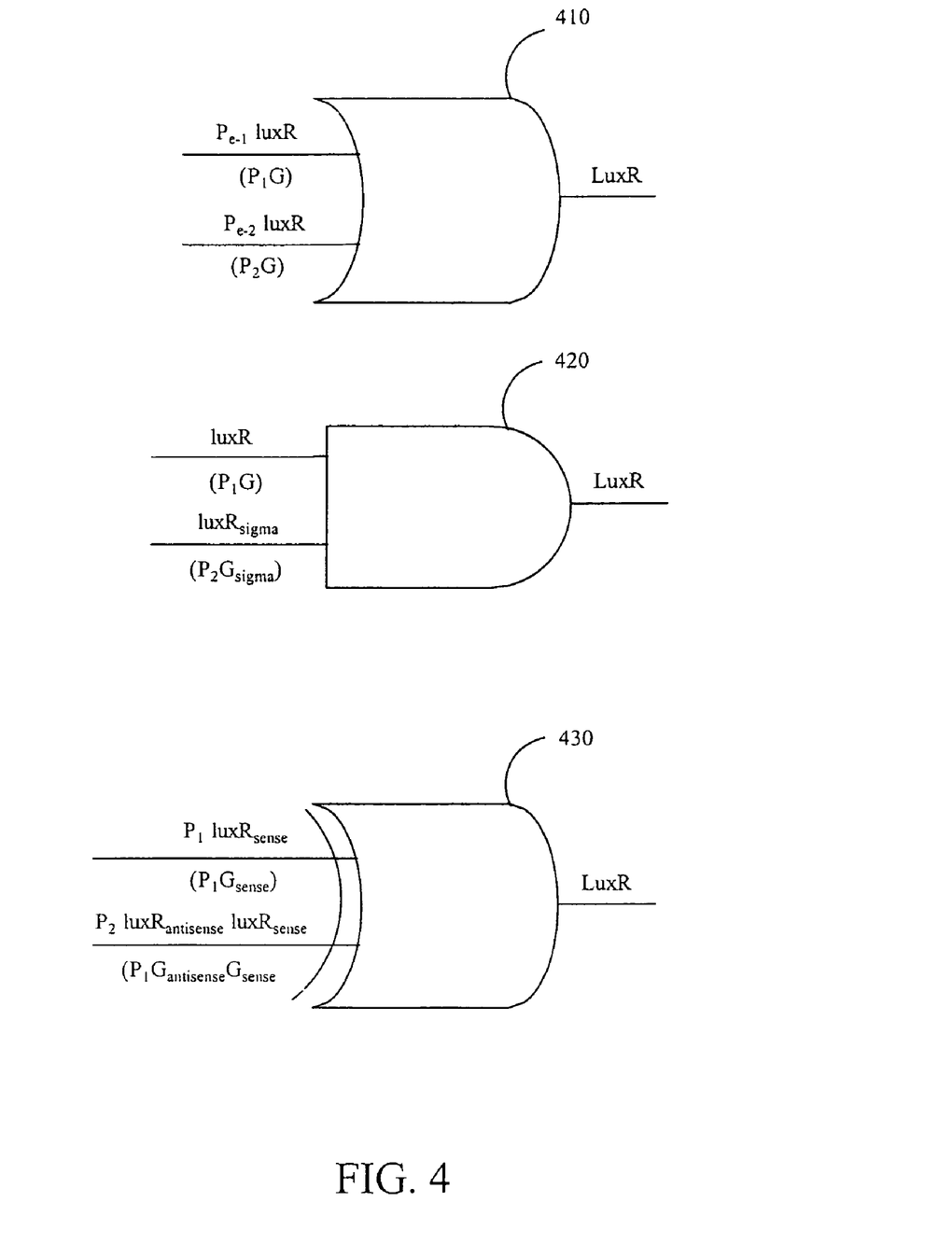
FIG. 4 Illustrates various cell-based logic gates shown in FIGS. 1–3 formed using the luxR gene, according to an embodiment of the invention.

FIG. 4 illustrates embodiments for the biochemical logic gates OR 410, AND 420 and XOR 430 shown in FIGS. 1–3 using the luxR gene coding for the LuxR gene product. All three gates can be supported by a single cell which may then be linked to other cells by diffusion of the diffusible element AHL.

When in-vivo logic gates are linked together, the cells can transmit, receive and process signals to and from each other. For example, gates can be linked when an output product from one logic gate diffuses to a second logic gate and acts to stimulate an appropriate chemically inducible promoter. As one skilled in the art will realize, the ability to interconnect devices permits formation of latched devices (e.g. flip-flops), digital counters and even more complex combinatorial devices (microprocessors). As in the use of basic gates, in a preferred embodiment, gene-expressed output products preferably display bioluminescence and are detected by the presence or absence of luminescence by an appropriate optical detector (e.g. CCD).

Since states of the various devices described are based on the formation of a gene product, it is clear that a memory device can be formed from a matrix of such devices or similar cellular devices. Memory devices can be volatile memory devices which require application of an input energy source or chemical to hold information, or a non-volatile memory which does not require an input to hold stored information. For example, the presence of a particular gene product can represent a "1" state, while the absence of the particular gene product can represent the "0" state. Thus, a non-volatile read only memory can be formed from an initial programming cycle where desired bits are placed in the "1" state through appropriate inducement to result in the production of a gene product. Bits may be erased in numerous ways depending on the particular cells used. For example, radiation, temperature and various chemical stimuli can be used to turn off bits comprising a memory device. In one embodiment of a memory device, the gene product confers a bioluminescent product and a CCD detector is used to "read" the memory.

The in-vivo logic circuitry disclosed can support a wide range of applications. The applications can include drug and biomaterial manufacturing, programmed therapeutics, embedded intelligence in materials, sensor/effector arrays, gene therapy, and nanoscale fabrication.

A given device can be formed from multiple cell types. For example, a device can include cells from different bacterial strains, species types and/or different genera. It is also possible to use hybrid prokaryote and eukaryote systems, such as yeast and bacterial cells. Interconnectivity can be established using pheromones or mating factors. Placement of specific cells in predetermined locations will allow pixelized mapping of an output signal, such as through use of light emitted from bioluminescent products and detected by CCD cameras.

Although described above as employing chemical inducers, it may be preferable in some applications of the invention for some promoters to be inducible by electromagnetic energy, such as electrical current. For example, gate-gate chemical connectivity via chemical diffusion (e.g. AHL diffusion) can be interfaced with electrical promoter stimulation in devices. Individual gates can be formed which are responsive to electrical stimulation for all gate inputs. Alternatively and generally preferably, gates can be responsive to chemical stimulation of one or more inputs and electrical stimulation of one or more other inputs. Use of electrically inducible promoters permits interfacing cells with electronic integrated circuits.

EXAMPLES

The following examples are included to demonstrate several preferred embodiments of the invention. It should be appreciated by those having skill in the art that the techniques disclosed in the examples which follow represent techniques discovered by the inventors to function well in the practice of the invention, and thus can be considered to constitute preferred modes for its practice. However, those skilled in the art should, in light of the present disclosure, appreciate that many changes can be made in the specific embodiments which are disclosed and still obtain a like or similar result without departing from the spirit and scope of the invention.

Example #1

Biosensor Device

A whole cell biosensor device can be formed using the invention to be deployed in a microenvironment of MEMS or microfluidic devices, or a collection of these devices in a multi-chip module (MCM) or distributed wireless network. The biosensor device can respond to one or more specific chemical and/or physical inputs (e.g. heat or electrical current), accessing a small part of the DNA memory of the cell by addressing a particular promoter, generating outputs in the form of polypeptides, and communicating with a physical transducer through calorimetric, electrochemical, or preferably bioluminescence means. The biosensor device can be utilized to address complex sensing and information extraction problems in areas such as complex environmental monitoring such as wastewater diagnostics and bioprocessing. The biosensor device can also be used as a medical diagnostics and disease management device in the form of an implantable sensor. The massive parallel interconnectivity of a population of whole cells, can provide the biosensor with information processing ability for computational intensive applications such as weather forecasting.

This invention is contemplated to be useful for covert monitoring of chemical manufacturing plants suspected of producing chemical weapons or biological weapons. A series of logic gates which each respond to specific products found in waste streams in a sequential process could allow devices produced using the invention to sense the presence of chemical agents and permit intelligence authorities to be notified when such chemical agents are being produced.

In a preferred embodiment, the biosensor employs electrically conductive nanofibers disposed on an integrated circuit configured to permit independent biasing of respective nanofibers. Unless biased by the underlying integrated circuit, nanofibers float. This configuration permits electrical current to be directed across specific cells in an array of cells, the electrical current flowing between nanofibers biased at different potentials, across one or more whole cells making up the biosensor device. The nanofiber material selected is preferably non-toxic to cellular material, such as graphite, and capable of selective deposition on the integrated circuit surface. See V. I. Merkulov, D. H. Lowndes, Y. Y. Wei and G. Eres, Patterned Growth of Individual and Multiple Vertically Aligned Carbon Nanofibers, Applied Physics Letters, Vol. 76, No. 24 3555–3557, June 2000; V. I. Merkulov, M. A. Guillorn, D. H. Lowndes and M. L. Simpson, Shaping Carbon Nanostructures by Controlling the Synthesis Process, Applied Physics Letters, Vol. 79, No. 8 1178–1180, August 2001. Both of the above references are hereby incorporated by reference into this application in their entirety.

Cells can preferably be encapsuled in latex or a similar material prior to being placed on the IC. After the vertically aligned carbon nanofibers are selectively grown on the surface of the IC, the encapsulated cells can preferably be pipetted (or similar method) onto the IC chip. Cells would then be trapped between nanofibers.

If desired, using available micro-placement techniques, different cells can be placed in different locations on the IC to produce devices having varying characteristics. For example, ink jet printers can be used to place different biological materials such as cells on chips in designated locations with a resolution on the order of microns.

Information may be sensed in a variety of ways. Cells can monitor their environment and take in chemical information or physical information. For example, gene regulation can be changed by the presence of certain chemical, light, temperature and similar environmental factors. The IC chip interfaced with the biological material can also take in information. The IC can measure parameters such as pH and temperature.

Information is derived in two general formats, a first format in the cells and a second format on the IC chip. Information processing algorithms can be cell based on cellular logic or based on conventional IC chip logic. As information is derived, the information (e.g. cellular) can be ported to a designated place (e.g. IC chip) for processing.

Regardless of the form in which the signal is received by the biosensor device, the information delivered is processed by the system for the chosen algorithm. For example, in a biosensor device receiving chemical sensor information, the information comes into the system when the targeted chemical upregulates (i.e. increases) the expression of a gene cassette. A simple algorithm performed by the system is to measure and report the magnitude of the upregulation, such as the IC measuring the amount of light emitted by a cell and determining the concentration of a given chemical on the basis of the measured emitted light. For example, the biosensor can be used to determine the presence and concentration of environmentally supplied chemical toxins. The IC of the biosensor device preferably performs this algorithm.

Example #2

Current Inducible Promoters in *E. coli*

Metabolic and information networks and adaptive responses used by microorganisms such as *E. coli* in response to environmental stimuli are used to form the basis of logic circuits. A controllable stimuli is used to communicate with the selected cells. Output signals generated contain information regarding the network process performed. A measurement structure detects the output signal generated. Individual discrete logic devices can be readily linked to form integrated devices through the process of chemical diffusion.

The molecular basis for intercellular communication among cells of a specific bacterial species is well established. Often such communication, termed "quorum sensing", is associated with cell density dependent synthesis of signaling (or quorum sensing) chemicals that activate regulatory genes controlling various operons within prokaryotic cells. A principle model of quorum sensing for bacterial bioluminescence is observed in the marine bacterium *Vibrio fischeri*. However, variations on this model and analogous systems are widely distributed among many bacterial species. Quorum sensing permits coordinated physiological activity and growth among cells to exploit a given, perhaps optimal, set of environmental or ecological conditions.

Figure 5:
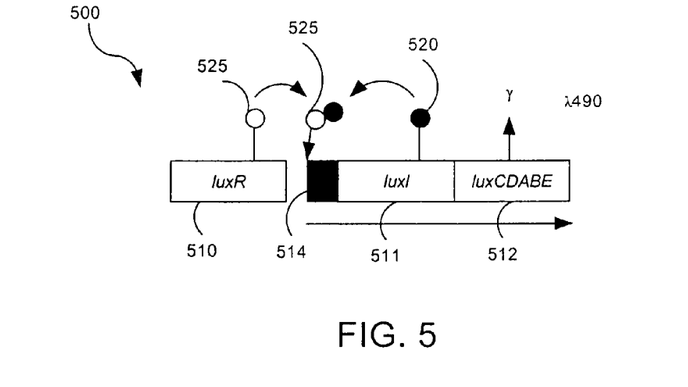
FIG. 5 Illustrates a molecular biological model where the gene sequences are represented by boxes, the small circles represent the expressed regulatory elements for luxR (open circles) and luxI (solid circles) genes, according to an embodiment of the invention.

In bacterial bioluminescence, the capacity of these cells to produce light can result from incorporation of the lux genes, which are responsible for bioluminescence in bacteria such as the marine bacterium *Vibrio fischeri*. FIG. 5 is a schematic representation 500 of the lux genes, showing positive regulation of these genes by the LuxI and LuxR gene products. The luciferase genes (luxAB) encode proteins responsible for generating bioluminescence while the reductase (luxC), transferase (luxD), and synthetase (luxE) genes code for proteins involved in producing an aldehyde substrate required in the bioluminescent reaction. In FIG. 5, the gene sequences 510, 511 and 512 are represented by open boxes. The small circles 515 and 520 represent the expressed regulatory elements of the luxR 510 and luxI 511 gene. The expressed product 520 of the luxI gene 511 is acyl-homoserine lactone (AHL) synthetase. Its product, acyl homoserine lactone (AHL), acts as an inducer of the bioluminescent reaction. AHL 520, represented by black circles, forms a complex with the expressed product 515 of the luxR gene, i.e. luxR transcriptional regulator 515 (white circles). This complex 525 (black and white circles) binds to the promoter site 514 of the luxI gene 511 (black box). Transcription is induced, in the direction of the lower arrow, of luxI 511 and luxCDABE 512, which code for the proteins that carry out the biochemical reactions resulting in the emission of 490 nm light 530. This mechanism of positive regulation of the lux operon by the luxR-AHL complex 525 occurs both in native *Vibrio fischeri* and in recombinantly introduced lux gene cassette in bioreporter cells.

Light generation in *Vibrio* and in the bioreporter cells is amplified by a mechanism known as autoinduction. The luxI gene results in production of AHL, which diffuses into the extracellular environment where at a threshold concentration it induces lux and luxCDABE transcription of neighboring bioluminescent cells and itself, in a cascade effect that ultimately generates intense bioluminescence from the group of cells. The effect of the autoinduction mechanism is to amplify significantly the production of light, by engaging a large number of cells in the effort. The present invention can utilize autoinduction to amplify the production of light by genetically engineered lux-based bioluminescent bioreporter cells.

All of these genes have been engineered separately and can be mixed and matched for broad biotechnical applications. Homologs of the luxR/I system have been identified in numerous bacterial species. The regulatory protein LuxR can represented as $LuxR_{1,2,3,n}$ indicating that distinct proteins exist that interact with discrete and in some bases multiple AHLs. LuxI can be represented as $LuxI_{1,2,3,n}$ indicating that various AHL synthetases are produced ($AHL_{1,2,3,n}$) capable of interaction with different luxRs. luxCDABE are the minimal required genes for the intrinsic bioluminescent reaction capable of producing light with no exogenous substrates. The gene luxAB encodes the heterodimeric luciferase mediating a monoosygenase oxidation of $FMNH_2$ and myristaldehyde to produce the excited reaction product with subsequent light emission and formation of FMN and myristic acid. luxCDE constitutes a gene set for recycling myristic acid to the myristaldehyde reactant pool.

Genes other than the lux gene may be used with the invention to produce bioluminescent gene products, such as the firefly luciferase (LUC) gene, the LUC gene primarily used for eukaryotic logic gates. Accessory pigments or photoproteins such as the Green Fluorescent Protein (GFP) can also be used for wave shifting by photons from the bioluminescent reaction with concomitant excitation and subsequent emission at a somewhat longer wavelength. Mutant GFPs may be obtained that are red shifted to optimize excitation at 488 nm with subsequent emission at 507 nm (bioluminescence). Shifts in wavelength result from amino acid substitutions in the chromophore region of the protein.

Figure 6:
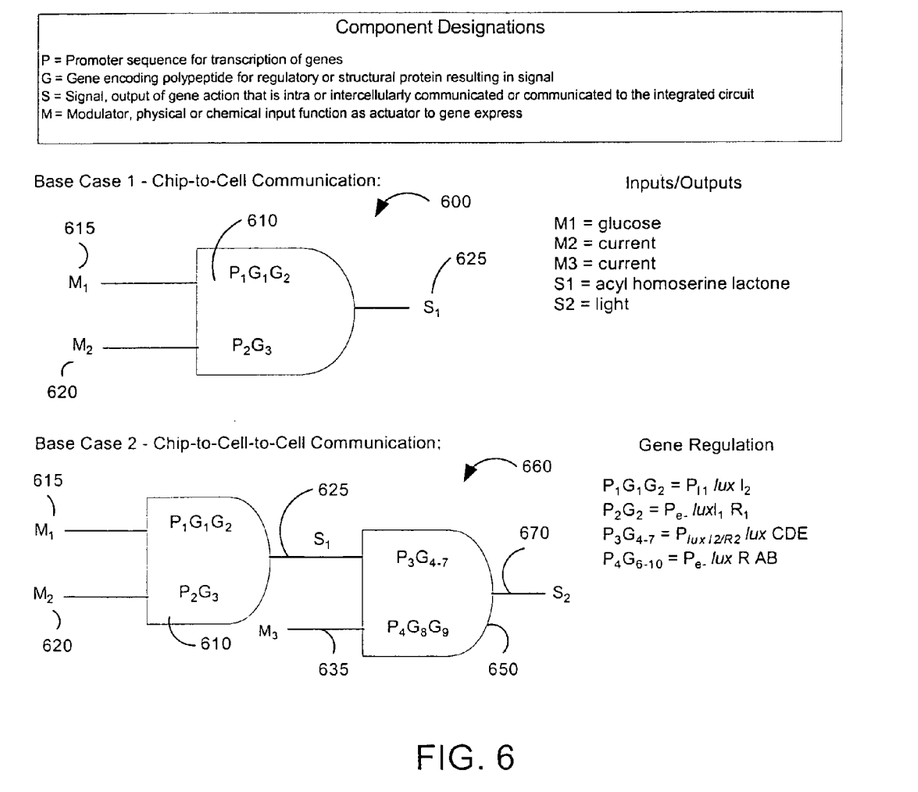
FIG. 6 Illustrates chip-to-cell communication and chip-to-cell-to-cell communication, according to an embodiment of the invention.

A basic design of a chip-to-cell (base case 1) 600 and chip-to-cell-to-cell (Base case 2) 620 cell based communication circuit is illustrated in FIG. 6. Base case 1 600 demonstrates actuator inputs 615 and 620 of an energy source being electrical current 620 from an electronic IC chip along with glucose 515 to the host cell 610. Electrical current may be employed to stimulate specific promoters that induce genes to express certain proteins that form a luxI/R complex which in turn induces expression of the $LuxI_2$ protein.

The resulting $LuxI_2$ protein synthesizes AHL (S1) 625 which diffuses from the host cell 610 to a second cell 650 creating cell-cell communication, represented as the second logic circuit 660 shown as Base case 2 in FIG. 6. The second cell 650 only produces light when electrical current 635 induces the luxAB gene to express the $LuxR_2$ protein. The resultant $LuxR_2$ proteins interact with the diffusible AHL 625 and positively regulates the luxCDABE operon. Cell 650 can then express a protein which emits light 670 that can be detected and monitored by an appropriate detector, such as an optically sensitive integrated circuit.

Example #3

Combinatorial Functions with Cell Based Logic

Figure 7:
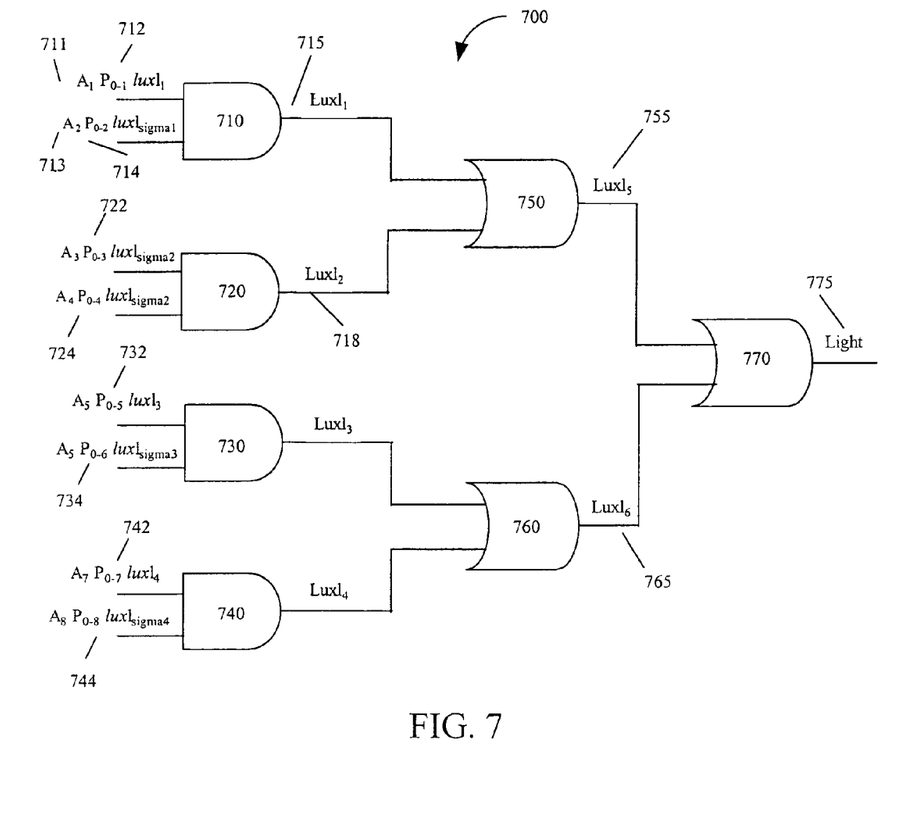
FIG. 7 Illustrates a multiplexer circuit using cell-based logic gates, the gates interconnected by chemical diffusion, according to an embodiment of the invention.

Logic modules described in Example 2 were combined into an interconnected multiplexer circuit 700 by adding the quorum sensing element luxI coding for the LuxI gene product as shown in FIG. 7.

The first components in the circuit shown are composed of four (4) AND gates 710, 720, 730 and 740 under control of current inducible promoters ($P_{e-1}$ to $P_{e-8}$). When electrical current is supplied at $A_1$ 711, the $P_{e-1}$ promoter 712 is stimulated to transcribe the luxI, messenger RNA (mRNA) in gate 710 only if the transcriptional sigma factor is present which is activated by electrical current supplied at $A_2$ 713 applied to a second current inducible promoter $P_{e-2}$ 714. The sigma factor is a protein that binds to the RNA polymerase to allow recognition of a particular promoter. The overall effect at cell 710 is that if, and only if, both $P_{e-1}$ and $P_{e-2}$ are stimulated, synthesis of $LuxI_1$ 715, will occur. If either $P_{e-1}$ or $P_{e-2}$ are not stimulated, synthesized of LuxI 715, will not occur.

If synthesized, LuxI 715 induces the expression of AHL, the AHL being a freely diffusible product which arrives at the next cell in series, cell 750, which functions as an OR gate. In this cell two genetic constructions are present: $P_cluxR_1$ codes for the $luxR_1$ under the control of a constitutive promoter $P_c$, As used herein, constitutive means gene expression occurs at certain predetermined level which is neither up-regulated or down-regulated. $luxI_5$ codes for $LuxI_5$ 755 which is synthesized only if either of the proteins $LuxI_1$ 715 or $LuxI_2$ 718 are synthesized.

A similar series of AND and OR gates converges from the current inducible promoters $P_{e-5\ to\ e-8}$ (732, 734, 742 and 744) to yield LuxI$_6$ 765 from cell 760. The signal output from OR gates 750 and 760 converge on cell 770 which also functions as an OR gate. If either LuxI$_5$ 755 or LuxI$_6$ 765 are synthesized, those proteins will induce the production of AHL which will diffuse to at cell 775. AHL will interact with the LuxRI gene product which in turn will induce synthesis of the associated lux structural proteins, the lux structural proteins producing light emission 775 which can be readily detected by an appropriate optical detector.

Example #4

Cell-to-Cell Communication Circuits

Figure 8:
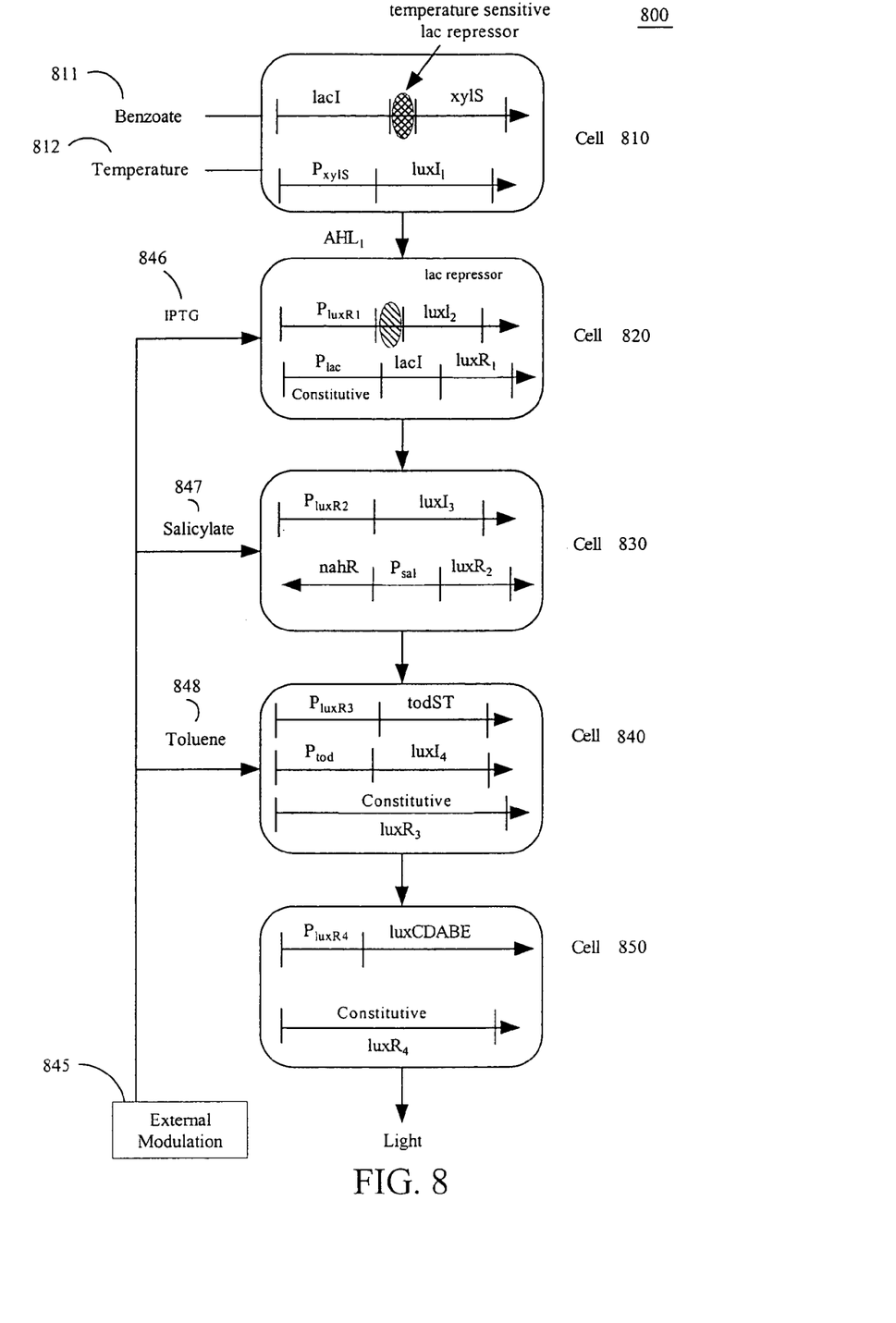
FIG. 8 Illustrates transcription modulators connected in series for the transference of input signals to a light output signal, according to an embodiment of the invention.

Cell-to-Cell logic circuits can utilize quorum sensing communication capabilities linked to the activation of regulatory genes for the control of specific genetically engineered operons. A complete cell-cell logic circuit 800 design is illustrated in FIG. 8, whose basis relies on signal transference via luxI derived AHL autoinducer interactions with luxR proteins. The advantage in using AHL autoinducers as signaling elements is that they remain specific in their interaction with the regulatory protein LuxR. Therefore, luxI$_j$ synthesizes AHL$_1$ which specifically interacts with luxR$_1$. In this manner, a whole-cell circuit can be designed in which activation occurs in a stepwise fashion, with each cell in the series dependent on the signal molecule produced from the cell before.

Additionally, since the transducers are diffusible signal molecules, no hardwire interconnects are required. In the example presented here, the first microbial population in the series, denoted here as a single cell, cell 850, is exposed to two inputs, benzoate 811 and temperature 812, both of which must be present for cellular activation. Benzoate can be supplied from sodium benzoate solution. An increase in temperature from ambient to approximately 32° C. deactivates the temperature sensitive lac repressor protein which was previously blocking transcription of the xyIS gene. Heat can be provided by thermal pads. Benzoate can be provided by application of a benzoate containing solution, such as sodium benzoate, preferably using microfluidics. This allows the xyIS gene protein product XyIS to be transcribed. Concurrently, the addition of benzoate 811 and its subsequent interaction with XyIS activates the promoter $P_{xyIS}$, thereby inducing transcription of luxI$_1$.

The protein product of the luxI$_1$ gene is the AHL synthetase LuxI$_1$ which yields the diffusible signal molecule AHL$_1$. AHL$_1$ subsequently diffuses out from the Cell 810 and into any of the other cells 820, 830, 840 and 850 within the circuit. However, due to its specific binding with luxR$_1$, its only successful interaction can occur in Cell 820, where it induces $P_{luxR}{}^1$ to initiate transcription only of LuxR$_1$. Note that every cell in the circuit is designed similarly; such that a diffusible AHL molecule released from one cell is only capable only of interacting with one other cell type in the circuit. Thus, the communication system proceeds logically in a stepwise series fashion to result in expression of an end product which produces visible light generation.

In addition to diffusible AHL signal molecules, Cells 820, 830 and 840 also require a secondary input for complete genetic activation. This secondary level of control is provided by external modulators 845, which can be supplied by microfluidics. In Cell 820, for example, the introduction of the compound isopropyl β-D-thiogalactopyranoside (IPTG) 846 to the cellular medium de-activates lac repression, thereby allowing transcription from $P_{luxR}{}^1$ (if and only if AHL$_j$ is also present) to produce the protein LuxI$_2$. The addition of salicylate to Cell 830 and toluene 848 to Cell 840 functions similarly as a secondary level of control in the logic circuit to fully ensure that cellular activation occurs only in a stepwise serial manner.

Cell 850 represents the final cell in the logic circuit series 800 shown by FIG. 8. This cell receives AHL$_4$ which interacts with luxR$_4$ to induce transcription of the luxCD-ABE operon. Since the complete lux operon is represented within this cell 850, no additional requirement for exogenous chemicals or co-factors is required. Thus, Cell 850 remains completely self-sufficient in its ability to generate a visible light response.

Figure 9:
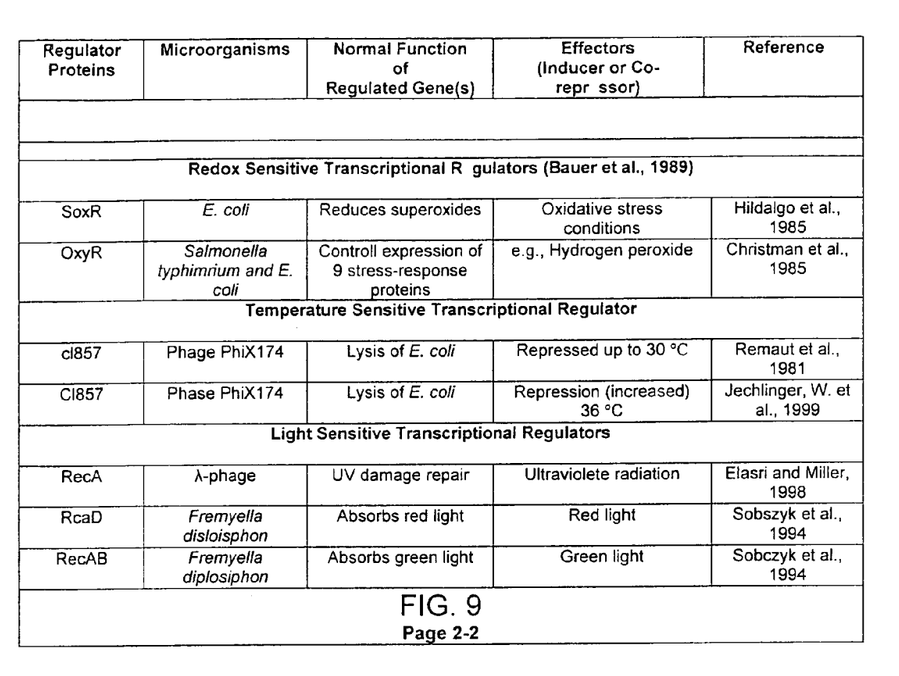
FIG. 9 Illustrates a potential target regulator gene system for construction of cell-to-cell communication networks, according to an embodiment of the invention.

It is noted that the invention can be used with many other promoter sequences. For example, by utilizing any of the inducible promoter sequences listed in FIG. 9, a vast array of other regulatory systems can be incorporated into a functional logic circuit.

Example 5

Chip-to-Cell Communication Circuits

There are two basic components for the utilization of living cells in data processing linked with an electronic IC, the cells and the electronics to which they are interfaced. Cells are subjected to an input, the cells then provide an output to the IC. The IC can then interpret the output of the cell and responsively provide a signal directed back to the cell. This succession of inputs and outputs results in a series of computations to ultimately provide a final output.

The system can consist of bioreporters on an IC that can analyze a three-component mixture of mixture of compounds (salicylate, tricholorethylene (TCE), and benzoate) to individually ascertain its composition. The bioreporter(s) can consist either of a population of three genetically-engineered cells, each containing separate bioluminescent reporter constructs, or a single microorganism containing all three lux fusions.

In this example, the IC has an integrated photodector and polysilicon heating pads to allow for temperature control. The organism(s) contain three lux fusions: 1) tod-lux using the *Vibrio fischeri* (30° C.) lux cassette (target analyte TCE) (Applegate, B. M., S. R. Kehrmeyer, and G. S. Sayler. 1998. A Chromosomally Based tod-luxCDABE Whole-Cell Bioluminescent Reporter for Benzene, Toluene, Ethylbenzene, and Xylene (BTEX) Sensing. Applied and Environmental Microbiology. 64: 2730–2735; Shingleton, J. T., B. M. Applegate, A. C. Nagel, P. R. Bienkowski, and G. S. Sayler. 1998. Induction of the tod Operon by trichloroethylene in *Pseudomonas putida* TVA8. Applied and Environmental Microbiology. 64:5049–5052.) tol-lux (XY1S regulated promoter (Burlage et al., 1989) using the *Vibrio harveyii* (37° C.) lux cassette (target analyte benzoate), and 3) sal-lux *Xenorhabadus luminescens* (42° C.) lux cassette (target analyte salicylate), which are independently upregulated in the presence of their target analyte. The above three (3) references are hereby incorporated by reference into this application in their entirety. It is known that significant bioluminescence will not be detected above the indicated temperatures. The tol-lux strain contains a binding site for the temperature dependent modified lac repressor LAP267, which only allows for the expression of the lux fusion between 32° C. and 39.5° C. The sal-lux operon will also contain a binding site for the lambda repressor protein which will be constitutively expressed in this cell line to inhibit the tol-lux fusion. It is known that the lambda repressor also inhibits expression of the sal-lux fusion below 42° C. Cells can be placed on the IC and tested against various combinations of the three analytes.

Figure 10:
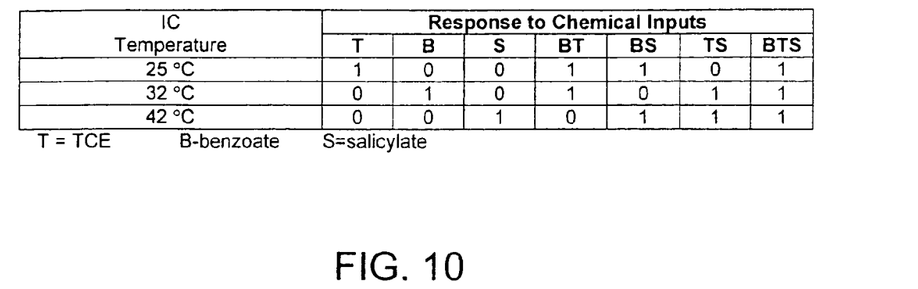
FIG. 10 Illustrates a truth table for cell/thermal processor, according to an embodiment of the invention.
Figure 11:
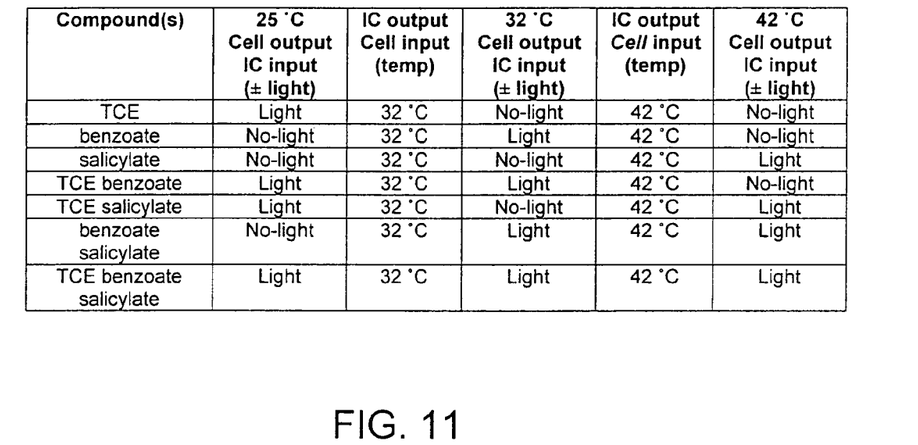
FIG. 11 Illustrates input/output parameters for the cell/thermal processor circuit, according to an embodiment of the invention.

In this example, the output from the bacteria (bioluminescence) can be detected by the IC. Upon detection of the bioluminescence, the chip can provide feedback to the bioreporter in the form of a step wise increase in temperature (25° C., 32° C., 42° C.). It is known that the thermal instability of the various lux gene cassettes can provide signal discrimination along with the temperature regulated repressors. The expected inputs and outputs of this particular bacteria/electronic interface can be seen in FIG. 10. The actual inputs applied and outputs observed (temperature and bioluminescent signals) are shown in FIG. 11. The series of light outputs detectable at each temperature step provides the necessary information to discriminate the individual analytes within the mixture.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

We claim:

1. A method comprising the steps of:
providing a plurality of genetically engineered cells, said genetically engineered cells having at least one transcriptional unit, said transcriptional unit comprising a gene and a promoter, wherein application of a stimulus to said promoter results in the expression of a gene product;
applying a plurality of independent input signals via nanofibers to said plurality of genetically engineered cells, said input signals being an energetic or chemical stimulus to activate said promoter, and
detecting for the presence of at least one output signal, said output signal being related to a presence of said gene product.

2. The method of claim 1, wherein said energetic stimulus comprises electrical current, said promoter including at least one current inducible promoter.

3. The method of claim 1, wherein said at least one transcriptional unit comprises a plurality of transcriptional units, said plurality of transcriptional units configured to form a plurality of interconnected logic gates, further comprising the step of chemically communicating information between respective logic gates.

4. The method of claim 3, further comprising the step of electrically inducing expression of a first gene product from a first logic gate, wherein said first gene product induces production of at least one diffusible product which induces expression of gene products from at least one other of said logic gates.

5. The method of claim 1, wherein said gene product confers a bioluminescent output.

6. The method of claim 1, wherein said at least one transcriptional unit comprises a plurality of transcriptional units, said applying step comprising independently controlling application of said energetic or chemical stimulus to said plurality of transcriptional units.

7. The method of claim 6, wherein said applying step comprises application of electrical current to at least one of said plurality of transcriptional units.

8. A method comprising the steps of:
providing at least one genetically engineered cell, said genetically engineered cell having a plurality of transcriptional units configured to form a plurality of interconnected logic gates, said transcriptional units comprising a gene and a promoter, wherein application of a stimulus to said promoter results in the expression of a gene product;
applying at least one input signal to activate said promoter;
chemically communicating information between respective logic gates without the use of electrical current; and
detecting for the presence of at least one output signal, said output signal related to a presence of said gene product.

9. The method of claim 8, wherein said stimulus comprises electrical current, said promoter including at least one current inducible promoter.

10. The method of claim 9, further comprising the step of electrically inducing expression of a first gene product from a first logic gate, wherein said first gene product induces production of at least one diffusible product which induces expression of a gene product from at least one other of said logic gates.

11. A method comprising the steps of:
(a) providing a first cell comprising a first logic gate comprising a first transcriptional unit comprising a first gene and a first promoter;
(b) providing a second cell in electrical or chemical communication with the first cell, the second cell comprising a second logic gate comprising a second transcriptional unit differing from the first transcriptional unit and comprising a second gene and a second promoter;
(c) applying a stimulus corresponding to an input datum to the first cell but not the second cell, the stimulus causing modulation of expression of the first gene, wherein the modulation results in the production of a first output signal that acts on the second cell to modulate expression of the second gene to result in the production of a second output signal corresponding to the output datum; and
(d) analyzing the second cell for the presence of the second output signal.

12. The method of claim 11, wherein the first cell is connected to an integrated circuit chip that provides the stimulus.

13. The method of claim 11, wherein the first logic gate is an OR logic gate.

14. The method of claim 11, wherein the first logic gate is an AND logic gate.

15. The method of claim 11, wherein the first logic gate is an XOR logic gate.

16. The method of claim 11, wherein the stimulus comprises electrical current and the first promoter is a current-inducible promoter.

17. The method of claim 11, wherein the first output signal comprises a diffusible molecule.

18. The method of claim 11, wherein the first output signal comprises emission of light.

19. A method comprising the steps of:
(a) providing a first cell comprising a first logic gate comprising a first transcriptional unit comprising a first gene and a first promoter, and a second transcriptional unit differing from the first transcriptional unit and comprising a second gene and second promoter;
(b) providing a second cell in electrical or chemical communication with the first cell, the second cell comprising a second logic gate comprising a third transcriptional unit differing from the first or second transcriptional unit and comprising a third gene and a third promoter, and a fourth transcriptional unit differing from the third transcriptional unit and comprising a fourth gene and a fourth promoter;

(c) applying a stimulus corresponding to an input datum to the first cell but not the second cell, the stimulus causing modulation of expression of at least one selected from the group consisting of the first gene and the second gene; wherein the modulation results in the production of a first output signal that acts on the second cell to modulate expression of at least one selected from the group consisting of the third gene and the fourth gene to result in the production of a second output signal corresponding to the output datum; and (d) analyzing the second cell for the presence of the second output signal.

20. The method of claim 19, wherein the first cell is connected to an integrated circuit chip that provides the stimulus.

21. The method of claim 19, wherein the first logic gate is an OR logic gate.

22. The method of claim 19, wherein the first logic gate is an AND logic gate.

23. The method of claim 19, wherein the first logic gate is an XOR logic gate.

24. The method of claim 19, wherein the stimulus comprises electrical current and the first promoter is a current-inducible promoter.

25. The method of claim 19, wherein the first output signal comprises a diffusible molecule.

26. The method of claim 19, wherein the first output signal comprises emission of light.

* * * * *